United States Patent
Redmond et al.

(10) Patent No.: US 6,818,232 B1
(45) Date of Patent: Nov. 16, 2004

(54) OAT EXTRACTS: REFINING, COMPOSITIONS AND METHODS OF USE

(75) Inventors: Mark J. Redmond, Edmonton (CA); David A. Fielder, Edmonton (CA)

(73) Assignee: Ceapro, Inc. (CA)

( * ) Notice: Subject to any disclaimer, the term of this patent is extended or adjusted under 35 U.S.C. 154(b) by 0 days.

(21) Appl. No.: 09/979,396

(22) PCT Filed: May 5, 2000

(86) PCT No.: PCT/EP00/04046

§ 371 (c)(1),
(2), (4) Date: Nov. 6, 2001

(87) PCT Pub. No.: WO00/67626

PCT Pub. Date: Nov. 16, 2000

(30) Foreign Application Priority Data

May 6, 1999 (EP) .............................. 99108965

(51) Int. Cl.⁷ ............................................... A61K 35/78
(52) U.S. Cl. ........................ 424/750; 426/622; 426/655; 426/656; 426/442; 426/506; 426/507; 514/568
(58) Field of Search ................................. 514/555, 568; 426/622, 436, 442, 460, 506, 507, 655, 656, 455; 424/750, 401

(56) References Cited

U.S. PATENT DOCUMENTS

| | | | |
|---|---|---|---|
| 4,028,468 A | | 6/1977 | Hohner et al. |
| 4,435,429 A | | 3/1984 | Burrows et al. |
| 5,034,227 A | * | 7/1991 | Nickel ...................... 424/195.1 |
| 5,312,636 A | * | 5/1994 | Myllymaki et al. .......... 426/417 |

FOREIGN PATENT DOCUMENTS

| | | | |
|---|---|---|---|
| EP | 0 449 557 A2 | 10/1991 | .......... A21D/13/02 |
| EP | 0 531 735 A1 | 3/1993 | ........... A61K/35/78 |
| EP | 0 661 047 A1 | 7/1995 | ......... A61K/31/135 |
| EP | 2 720 646 | 12/1995 | .......... A61K/35/78 |
| EP | 0 739 621 A1 | 10/1996 | ............ A61K/7/06 |
| GB | 1527101 | * 10/1978 | |

OTHER PUBLICATIONS

Diemar et al. Information on and determination of the antioxidant of oat flour. Z. Untersuch. Lebensm. 1940. vol. 79, p 23–42.*

Database WPI XP–002148926.

Database WPI XP–002148927.

XP–002148924–L. H. Dimberg, Olof Theander, and Hans Lingnert; Avenanthramides—A Group of Phenolic Antioxidants in Oats, vol. 70, No. 6, 1993; American Association of Cereal Chemists, Inc.

XP–002148925—F. W. Collins; Oat Phenolics: Avenathramides, Novel Substituted N–Cinnamoylanthranilate Alkaloids from Oat Groats and Hulls, 1989, p. 60–66, American Chemical Society.

* cited by examiner

*Primary Examiner*—Thurman K. Page
*Assistant Examiner*—Lakshmi Channavajjala
(74) *Attorney, Agent, or Firm*—Pendorf & Cutliff

(57) ABSTRACT

A simple and efficient method for the production of a stable, clear and high-potency oat extract, containing avenanthramide, is disclosed. The method employs the use of a differential dissociation constants and ultra filtration to stabilize extract, prevent the loss of functional activity as an anti-irritant and anti-oxidant.

9 Claims, No Drawings

OAT EXTRACTS: REFINING, COMPOSITIONS AND METHODS OF USE

A simple and efficient method for the production of stable, clear, high-potency oat extracts is disclosed. The method employs the use of differential dissociation constants and ultrafiltration to stabilise extracts, prevent hazing, and prevent the loss of functional activity as an anti-irritant and anti-oxidant. Also claimed are compositions of oat extracts derived from whole oat grains and oatmeal.

Further claims are made to compositions of oat extracts for use in cosmetic, nutraceutical, therapeutic medical and veterinary preparations.

FIELD OF THE INVENTION

The present invention relates to the production and use of solubilised, liquid oat extracts with formulations having utility in the personal care, cosmetics, nutraceutical, and pharmaceutical industries. More specifically the oat extract compositions of the present invention are useful as anti-irritants, anti-oxidants and skin-protection agents applied to the skin or when consumed.

BACKGROUND OF THE INVENTION

Oats (*Avena sativa*), and especially colloidal oatmeal suspensions have been used historically as adjuncts to the treatment of atopic dermatitis. It is desirable to extract the active ingredients from the oat in order to facilitate the use of the grain in medicinal and cosmetic applications.

Oat derivatives such as colloidal oatmeal, hydrolysed oat protein, oat starch, and β glucan have been used in the cosmetics and pharmaceutical industries as a skin protectant which provides a smooth feel after use. Specifically, the carbohydrates and protein in the oat derivatives have been known to function as a protectant to aid in enhancing the skin's barrier properties and thereby soothe the skin. Oat β glucans and lipids have also been known to function as emollients to lubricate and soothe the skin. For example, colloidal oatmeal has been used for bar soaps, bath powders, lotions, and poultices to treat skin that has been damaged, irritated, or distressed by a wide variety of causes. However, some oat derivatives, for example, colloidal oatmeal, are not fully soluble in aqueous solutions and leave undesirable residues on the skin and other surfaces. U.S. Pat. No. 5,219,340 describes a cloth applicator designed to retain colloidal oatmeal insoluble fractions.

Furthermore, hydrolysed oat protein undergoes processes such as hydrogenation, which may alter or adversely effect their properties. In particular, acid hydrolysed oat protein is known to have a strong odour which may adversely affect some consumer's acceptance of the product.

Liquid oat extracts prepared by extraction with alcohol, glycols, ethers, esters, mixtures, and aqueous mixtures thereof are typically unstable materials, which if not emulsified, readily separate into oil and aqueous phases which may further separate into soluble and insoluble phases. The loss of materials from solution results in hazing and the loss of functional activity. Haze is irreversible and the extract cannot be clarified by heat, dilution, addition of surfactants, or solvents or pH. Attempts to clarify the extracts using filtration resulted in the loss of functional activity. The instability of oat extracts has limited utility in cosmetic and medical applications.

Paton (1995) *Cosmetics and Toiletries* 110:63 describes the cosmetic use of oat extracts and provides information on cosmetic formulations. The oat extract described, OSTAR ARRIVEEN™, is produced from oats by a pearling process by which oat bran is obtained, which was then extracted with solvent. Charcoal was used in the process to clarify the preparation. The product is typically a dark brown coloured, non-homogeneous, bi-phasic extract. The utility of this product was limited by instability resulting in varying performance. The product could not be sterilised resulting in a high microbial load high due to non-kilned, non-stabilised oat bran.

Collins et al U.S. Pat. No. 5,169,660 describes the preparation of bran from cereal grains using aqueous alcohol extraction (83% w/w) and the recovery of crude by-products from waste through ion-exchange chromatography. The described process does not use pH pre-treatment or membrane filtration and so results in only recovered small quantities of by-product from waste. Utility is not described in cosmetic applications and pharmaceutical claims are not enabled. Collins on *Oats: Chemistry and technology* (1986) Ed. Webster AACC St. Paul, Minn. pp227–296 describes oat phenolic compound structure, occurrence and phytological function. Methods of extraction of these compounds and potential utility in the cosmetic and medical fields of use were not disclosed.

Onitsuka et al U.S. Pat. No. 5,716,605 describe the use of glycolic extracts of oats for the treatment and care of hair and the scalp. The extraction method described is different to the method of the present invention.

Cioca et al U.S. Pat. No. 5,552,135 describes improved sunscreen compositions including extracts from cereal plants. The primary extraction is made with chloroform or ethanol and further processed further in alcohol following evaporative concentration.

Hammonds et al PCF/US97/10724 describes fibrous sheet materials containing oat extracts to provide a soothing effect to the skin of the user. The oat extracts claimed are made by treating oats with extraction agents by methods known to those skilled in the art. Methods of preparing oat extracts are not disclosed; the described product used specific concentrations of OSTAR ARRIVEEN™ in the preferred mode.

Zimmerman U.S. Pat. No. 5,888,521 describes compositions for topical use consisting of hydroxycarboxylic acid and oat extract, and also relates to methods of enhancing the rate of skin desquamation. Methods of preparing oat extracts are not disclosed; the described product used specific concentrations of OSTAR ARRIVEEN™ in the preferred mode.

Roger et al U.S. Pat. No. 5,026,548 describes a phospholipid surfactant for use as a viscosity reducing agent in chocolate, or an emulsifier, surfactant or foam stabilizer in the food and other industries is produced by extracting oats using an alcohol such as ethanol or propanol, extracting the alcohol extract with methanol and evaporating the methanol.

Targan U.S. Pat. No. 5,468,491 describes a method for producing an aqueous oat syrup involving enzymatic digestion, cooking, filtration through on oat bed, and concentration to produce an extract composed of 80% sugars and 20% water. Utility is expressed as a flavour, colour, sweetener, and or texture enhancer. The composition is different to the present liquid oat extract.

Rouanet et al PCT/FR98/00826 describes a method for making a solid preparation of white colloidal oats, comprising the following steps: using cultivated oat seeds; stabilizing by at least one operation whereby dry vapour is injected followed by sudden cooling, preferably at about room temperature; pinning and drying; breaking and eliminating the bran; dimensional selecting of particles.

Vallet Mas et al EP 0 661 047 describes the combination of topical anti-histamines with solid oat flour to form an emulsion for the treatment of itching, reduction of inflammation and facilitation of spreading over the effected area. No reference is made to the anti-irritant potential of oat extracts, Kovacs EP 0 282 002 describes the use of combinations of nettle (Urtica) and oat extracts as food additives or pharmaceutical preparations. The methods of preparing the oat extracts are described as, "classical methods" and no enabling details are provided.

Lawrence U.S. Pat. No. 5,573,785 describes an oat derived, skin conditioning, cosmetic component produced by dispersing in water a water-soluble fibre composed of about 4 to 6 weight percent beta glucan, about 1 to 5 weight percent fat, about 80 to 94 weight percent carbohydrates and less than 8 weight percent protein. No data relating to anti-irritant and redness reduction is provided. Furthermore, composition is radically different.

The commercial uses of ultra-filtration are known to those skilled in the art. Uses include water purification, milk processing, fruit juice, and wine clarification. However, ultra-filtration cannot be used for processing oat extracts without first stabilising the product by reducing pH. The high oil content of oats compounds this problem.

Reverse osmosis is known to those skilled in the art for the production of water from salt solutions. The use of reverse osmosis for the concentration of alcoholic extracts and solvent recovery as described in the present invention is novel.

DISCLOSURE OF THE INVENTION

1. Primarily, the present invention provides a method for the production of an oat extract that offers several advantages over the known methods of extraction and enhances the properties of the extract.

Histological staining of intact oat kernels indicated that the phenolic compounds were located primarily in the aleurone layer of the oat kernel. This implied that enriched preparations of the functional compounds would best be made from bran obtained by conventional milling or debranning processes. We were surprised to discover that the maximum yield of Avenanthramides came from the whole oat, not a bran fraction.

The present invention is based on the discoveries that (a) the extraction of active ingredients from oat may be enhanced in terms of production and efficiency, and furthermore (b) the resulting extracts are stable for extended shelf-life periods and may be concentrated readily.

Thus, according to a first aspect of the present invention there is disclosed a method for producing of an oat extract comprising the following steps:
 a. Milling whole oats,
 b. Extracting the resulting oatmeal with a solvent,
 c. Adjusting the pH of the resulting oat extract to <4.0 (favorably <3.5),
 d. Membrane filtration (e.g. ultra-filtration) of the oat extract through a membrane <$10^4$ MWCO The oat extract produced according to the method of the present invention is quantifiable in terms of activity and certified product quality assurance can be given. In accordance with the invention, aqueous alcoholic extracts of whole oats or groats are refined to provide materials for use in cosmetic and pharmaceutical compositions such as creams, gels, powders, lotions, and the like.

The oat extract of the present invention preferably contains Avenanthramide (as defined below) at a concentration of between 1 and 1500 ppm of Avenanthramide, more preferably between 3 and 450 ppm of Avenanthramide, and most preferably between 15 and 150 ppm of Avenanthramide. Other compounds, for example phenolics, benzoic and cinnamic acids, flavones, flavonols, chalcones, flavanones, proanthocyanidins, aminophenolics, tocols, and saponins, are also found in the oat extract. These compounds may have utility as for example, anti-oxidants, sunscreens, and surfactants.

The oat extract according to the present invention contains no or very little amounts of β glucan, for example less than about 0.01%, and less than 0.01% protein of molecular weight greater than 10,000 Da.

Preferably in step d of the method according to the present invention the membrane filtration is an ultra-filtration.

Preferably, reverse osmosis is used to further concentrate and purify the oat extract obtained by step d.

In step b die solvent for extracting the oatmeal favorably comprises water and a primary alcohol. The primary alcohol is preferably selected from the group consisting of ethanol, methanol, propanol (n-, iso-), butanol (n-, iso-, tert-), or mixtures thereof. Ethanol:water is preferred.

The oat extract may be incorporated into a solvent for ease of handling. For example in a preferred embodiment, the oat extract is incorporated in a 1:1 w/w mixture of 1,3 butylene glycol and water.

The oat extract obtained according to the method of the present invention can be easily sterilised by heat, microfiltration, or irradiation (after step c or d).

2. According to a second aspect the present invention relates to therapeutic (pharmaceutical) or cosmetic compositions, in particular for treatment of skin, which may be formulated as solution, gel, lotion, cream, ointment, or other acceptable form.

The composition favorably comprises Avenanthramide in a concentration of between 0.01 and 150 ppm., more preferably between 0.01 and 50 ppm, even more preferably between 0.3 and 15 ppm, and most preferably between 1.5 and 4.5 ppm.

Equally favorable is a therapeutic or cosmetic composition comprising between 0.1 and 25 weight percent, preferably 1 and 10 percent, of an oat extract comprising Avenathramide in a concentration of, referring to the oat extract, between 1 and 1500 ppm, preferably 3 and 450 ppm of Avenanthramide. The oat extract comprised in the composition is preferably produced according to the method of the present invention (see 1. above).

The composition according to the second aspect of the present invention may also contain various known and conventional therapeutic and/or cosmetic ingredients providing they do not detrimentally affect the desired reduction of skin irritation. For example, cosmetic ingredients such as alcohols, fats and oils, surfactants, fatty acids, silicones, humectants, moisturisers, viscosity modifiers, emulsifiers, stabilisers, colourings agents, and perfumes or fragrances may be included.

The composition can be used as a dermatological cosmetic product, in particular for use in the treatment of sensitive skin and/or redness (and/or wrinkles of the skin and/or pigment spots).

Typically, therapeutic or cosmetic compositions according to the present invention are topically applied to the skin.

3. A third aspect of the present invention relates to the use of an oat extract which comprises Avenanthramide, preferably an oat extract
 (a) prepared according to the present invention and/or
 (b) comprising Avenathramide in a concentration as stated above, for the preparation of a topical dermatological therapeutic composition for treating erythema, pruritus, otitis, inflammations, irritations, and/or allergies affecting the skin, for the preparation of a topical dermatological composition with enhanced therapeutic effect for use in the treatment of disorder of skin and/or for the treatment of inflammations, and for the preparation of a topical dermatological composition with enhanced therapeutic effect for use in the treatment of disorder of skin and/or for the treatment of erythema, pruritus, otitis, inflammations, irritations, and/or allergies affecting the skin.

The use of the oat extract for the respective purposes corresponds to methods of imparting the respective therapeutic activity to a substance by adding a therapeutically effective amount of the oat extract 4. A fourth aspect of the present invention relates to Avenanthramide for use in the therapeutic treatment of disorder of skin and/or inflammations, This aspect corresponds to (a) a method for therapeutic treatment of disorder of skin and/or inflammations, comprising applying a therapeutically effective amount of Avenanthramide to the skin, preferably in form of an oat extract and/or formulated in a suitable carrier, (b) the substance(s) Avenanthramide for use in the therapeutic treatment of disorder of skin and/or inflammations, and (c) a therapeutic composition, in particular for treatment of disorder of skin and/or inflammations, comprising a therapeutically effective amount of Avenanthramide.

Details of therapeutic treatment are given below.

5. A fifth aspect of the present invention relates to an oat extract containing a minimum of 10 ppm of Avenanthramide, wherein the oat extract can be produced by a method comprising steps a–d as above, and the additional step e. Adjusting the concentration of Avenanthramide in the permeate after membrane filtration to >10 ppm

DETAILED DESCRIPTION OF THE INVENTION

The practise of the present invention will employ, unless otherwise indicated, conventional methods of chemistry, cereal chemistry, cosmetic chemistry, pharmacy, and biochemistry within the skill of the art.

All publications, patents and patent applications cited herein, whether supra or infra, are incorporated by reference in their entirety.

As used in this specification and the appended claims, the singular forms "a", "an", and "the" include the plural references unless the content clearly indicates otherwise. Thus the term "an Avenanthramide' can include more than one member of the group of Avenanthramides.

Definitions

In describing the present invention, the following terms are employed, and are intended to be defined as indicated below By an "Avenanthramide" in singular or plural is meant a member of a group of more than 36 naturally occurring anthranilic acid derivatives found in oats, and arm unique to cereal grains. Nomenclature follows the convention described in *Oats: Chemistry and technology* (1986) Ed. Webster AACC St. Paul, Minn. pp227–286 with specific Avenanthramide compounds by the prefix 'AF' followed by a number, for example AF-1, AF-2 and AF-6 as illustrated in FIG. 1 below.

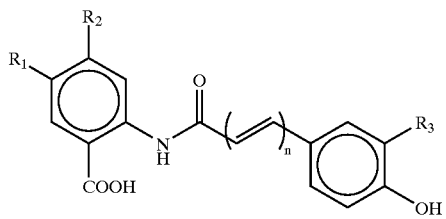

| Name | $R_1$ | $R_2$ | $R_3$ |
|------|-------|-------|-------|
| AF-1 | OH    | H     | H     |
| AF-2 | OH    | H     | $OCH_3$ |
| AF-6 | OH    | H     | OH    |

Formula 1. Avenanthramide Nomenclature and Structures

By "Oatmeal" is meant the product of grinding or milling whole naked (hulless) oats or oat groats.

By "Oat bran" is meant the product of grinding oat groats or rolled oats and separating the resulting oatmeal by sieving, bolting and/or other suitable means into fractions such that the oat bran fraction is not more than 50% of the starting material, and has a total β glucan content of at least 5.5% (dry weight basis) and a total dietary fibre content of at least 16.0%.

By "Oat flour" is meant the product of grinding oat groats or rolled oats and separating the resulting oatmeal by sieving, bolting and/or other suitable means into fractions that 100% of the flour passes through a 100 Mesh screen.

By "Ultra-filtration (UF)" is meant the process of tangential filtration whereby solutes are retained by a membrane the parameters of which are based on molecular weight By "Reverse Osmosis (RO)" is meant the process of tangential filtration whereby water and/or low molecular weight solvent, for example ethanol, passes through a membrane thereby concentrating the Retentate.

By "Membrane filtration" (MF) is meant the process of filtration whereby solutes are retained by a membrane the parameters of which are based on molecular weight. UF and RO are examples of MF.

By "Molecular Weight Cut-Off (MWCO)" is meant that above a specified MWCO, the membrane will retain most species of that molecular weight.

By "Permeate" is meant the fluid containing the solutes that passes through the UF/RO membrane.

By "Retentate" is meant the fluid containing the solutes that arc retained by the UF/RO membrane.

By "Flow" is meant the volumetric filtration rate (flow rate) through a given membrane area per unit time. Units are usually litres per square meter per hour (LMH).

By "Diafiltration" is meant the efficient method of recovering solutes (<MWCO) in low concentrations from the solution, by addition of fresh solvent at a rate equal to the UP rate. At constant volume, the permeate solutes are removed from the Retentate. The rate of recovery is a function of the UF rate and is independent of the concentration of the permeate solutes.

By "Membrane fouling" or "concentration polarization" is meant the accumulation of retained or absorbed material on the membrane surface.

By "Concentration" is meant the accumulation of rejected permeate solutes on the membrane By "Percent recovery" is meant the amount of desired solute as a percentage of the amount present in the feedstream.

General Methods

In accord with the present invention, an intermediate oat extract can be prepared by milling whole oats, extracting the oatmeal by mixing with a solvent, separating the resulting intermediate extract from the spent grain and adjusting the pH of the intermediate extract to <4.0 (preferably <3.5). The pH adjustment leads to high Avenanthramide yields in the extract.

Once extracted and acidified the intermediate oat extract is stable for several months.

The intermediate extract is subjected to membrane filtration, preferably ultra-filtration, whereby the filtrate of <10,000, more preferably <5,000 molecular weight is collected.

The resulting oat extract may be used for therapeutic or cosmetic purposes directly in alcohol. Alternatively it may be subjected to solvent exchange and the extract made up in a solvent of choice including, but not limited to, for example, butylene glycol, pentylene glycol, propylene glycol, glycerine, mixtures of these solvents, and combinations of these solvents or solvent mixtures with water.

The resulting oat extract is readily formulated as solution, gel, lotion, cream, ointment, or other pharmaceutically acceptable form. Preparations are formulated using methods known to those skilled in the art. For the reduction of erythema, the compositions should contain about 1–3% of the liquid oat extract (provided as a standardised 15 ppm Avenanthramide solution).

EXAMPLE 1

Oat Extract Preparation Process

Two or three replicates for each method were processed and analysed.

METHOD. Oat groats (Variety Hinoat) were ground through a Willey Mill to pass through a 10 Mesh screen. Oatmeal at a mixing ratio of 1:4 (w/v) oatmeal:solvent was added to a stirred solution of 50% (v/v) aqueous ethanol at 40 C. The resulting mixture was stirred for 30 minutes and then cooled to room temperature. The mixture was then centrifuged at 2830 g for seven minutes and the supernatant drawn off. The pellet was resuspended in fresh solvent and re-centrifuged. The supernatant was drawn off and the pellet re-suspended a third time in fresh solvent. All supernatants were combined and filtered through a course sintered glass filter.

To show the difference between the method (process) for producing an oat extract according to the present invention, which comprises die step of adjusting the pH of the extract to <4.0, and a method which does without pH adjustment, a comparison test series was carried out. Test samples were designated UF-B1, UF-B3, UF-C1, UF-C2, and UF-C3, respectively.

For samples of the I.D. series UF-B1 (comparison samples), in contrast to the method according to the present invention the oat extract was applied directly to the ultrafiltration module.

For samples of the series UF-B3, UF-C1, UF-C2, and UF-C3, in accord with the present invention the pH of the extract was adjusted to 2.5 with hydrochloric acid (1N) and ethanol added (~1%) to clarify the solution. The pale yellow extract was passed through a 0.45 μm filter (Gelman; Supor DCF) before ultrafiltration.

For ultrafiltration a Millipore Corporation MINI-PLATE™ Tangential-Flow Bioconcentrator (10,000 MWCO) was used. The unit contains a low protein binding YM membrane with a surface area of 108 cm$^2$. Pump rate was 1000 ml/min. and the flux (flow) was typically 14 L/m$^2$/h (LMH).

Weight profiles were conducted on the sample ID series UF-B by lyophilisation for 72 hours.

ANALYSIS High Performance Liquid Chromatography (HPLC) analysis was performed using a Thermo Separations Products (TSP) Spectra P4000 pump, a Varian column oven, and a Waters 991 Photodiode Array (PDA) detector with accompanying software. The column used was a CSC-Hypersil (5 μm, 120A, 0.46×25 cm-serial # 039775) at 25° C. UV monitoring at 330 nm was used. The flow rate was set at 1.0 ml/min.

All samples and standards were prepared in ethanol/water (1:1).

AF-1 standard (0.1 μg/μl): 5 μl injected Retention time: 23.68 minutes

AF-2 standard (0.1 μg/μl): 5 μl injected Retention time: 26.95 minutes

Avenanthramide fractions were prepared in 50% ethanol/water (5 ml) and 5 μl injected Table 1 describes the HPLC solvent program for the analysis of Avenanthramides.

TABLE 1

| Time (min.) | MeOH | H$_2$O | 5% Acetic Acid |
|---|---|---|---|
| 0 | 40 | 55 | 5 |
| 40 | 55 | 40 | 5 |
| 45 | 85 | 10 | 5 |
| 50 | 100 | 0 | 0 |
| 53 | 40 | 55 | 5 |
| 55 | 40 | 55 | 5 |

RESULTS As provided in Table 2 total Avenanthramides were calculated and expressed as AF-1 equivalents and recovery efficiency expressed as percentage recovery of Avenanthramides from the permeate are based on total Avenanthramides.

TABLE 2

| | UF Method | | | | | | |
|---|---|---|---|---|---|---|---|
| Sample I.D. | pH | Permeate | Retentate | Clean in place | Recovery | Diafiltration | Conc. polarization |
| UF-B1P | 7.5 | 33.8 | — | — | 57% | No | No |
| UF-B1R | 7.5 | — | 21.8 | — | 37% | No | No |

TABLE 2-continued

UF Method

| Sample I.D. | pH | Permeate | Retentate | Clean in place | Recovery | Diafiltration | Conc. polarization |
|---|---|---|---|---|---|---|---|
| UF-B3P | 2.5 | 45.5 | — | — | 77% | No | No |
| UF-B3R | 2.5 | — | 8.1 | — | 14% | No | No |
| UF-B3C | 2.5 | — | — | 1.1 | 2% | No | No |
| UF-C1P | 2.5 | 38.6 | — | — | 75–109% | Yes | No |
| UF-C2P | 2.5 | 43.3 | — | — | 84–122% | Yes | Yes |
| UF-C3P | 2.5 | 42.5 | — | — | 82–120% | Yes | Yes |

Notes:
1. Values based on AF-1 equivalents
2. Percent Avenanthramide recoveries of the permeate fraction for the C-Series are given as a range from UF-C1, C2, and C3 values Qualities of the Oat Extract 1. No haze formation has been observed in any oat permeate extracts produced to date.
2. Efficiency of the Avenanthramide extraction is >75%, more typically 85–100%.
3. The oat extract can be concentrated up to 50-fold without precipitation occurring.
4. The oat extract has low or no bacterial counts due to the permeate feed-stream being sterile before concentrating.
5. The oat permeate extract has a clean, clear yellow colour with a shelf life of more than 12 months.
6. The oat extract has a pleasant oat odour.
7. The permeate fraction was readily soluble at neutral pH in 35–70% ethanol/water.

EXAMPLE 2

Oat Extract Process Scale-Up

METHOD Oat groats (Variety AC Ernie) were ground through a Willey Mill to pass through a 10 Mesh screen seive. Oatmeal (1.5 kg) was added to a stirred solution of 50% (v/v) aqueous ethanol (6000 ml) at 40° C. The resulting mixture was stirred for 30 minutes and then cooled to room temperature. The mixture was then centrifuged at 2830 g for seven minutes and the supernatant drawn off. The pellet was resuspended in fresh solvent (3000 ml) and re-centrifuged. The supernatant was drawn-off and the pellet re-suspended a third time in fresh solvent (3000 ml). All supernatants were combined and filtered through a coarse sintered glass filter. The pH of the extract was adjusted to pH 3.5 with hydrochloric acid (1M) and ethanol added (~1%) to clarify the solution. The pale yellow extract was passed through a 0.45 $\mu$m filter (Gelman; Supor DCF) and made up to 12000 ml before ultrafiltration.

The extract was ultrafiltered at ambient temperature through a modified PES (Omega) T-screen membrane (0.09 m$^2$; 5000 MWCO, Pall Filtron) using a Pall Corporation CENTRASETTE™ unit. Flux rates (flow rates) ranged from 20–25 LMH. The pH of the resulting permeate was adjusted back to 6.5 with aqueous potassium hydroxide (5M).

A 200 ml aliquot was evaporated to dryness under reduced pressure and made up to 10 ml in 1:1 (v/v) aqueous ethanol. The solution was applied to a calibrated open column containing 100 mls. of LH-20 chromatographic gel (AP Biotech, Sweden) pre-equilibrated in ethanol:water:acetic acid (40:59:1). The column was washed with 2 Vb of solvent and the resulting fraction discarded. The Avenanthramides were eluted from the column with 2 bed volumes of 80% aqueous acetone. The sample was evaporated to dryness under reduced pressure and made up in 1:1 aqueous ethanol (5 ml). The sample was filtered through a 0.45 $\mu$m filter into a screw-capped vial for HPLC analysis.

ANALYSIS HPLC analysis for total Avenanthramides was conducted using a Thermo Separations Products (TSP) solvent delivery system and Hewlett Packard (HP) data collecting software on a C18 CSC HYPERSIL™ column (250×4.6 mm, 120 Å, 3 um). An HP photodiode array (PDA) detector monitoring from 190–400 nm, and specifically at 340 nm was used to detect all Avenanthramides. All peaks were integrated using retention times relative to an authentic AF-1 standard (obtained from Agriculture and Agri-Food Canada, ECORC, Ottawa, Canada). The solvent system consisted of acetonitrile, water, and aqueous 5% acetic acid as shown in Table 3.

TABLE 3

| Time (min.) | Acetonitrile | H2O | 5% Acetic Acid |
|---|---|---|---|
| 0–20 | 25 | 70 | 5 |
| 20–25 | 100 | 0 | 0 |
| 25–30 | 25 | 70 | 5 |
| 30–35 | 25 | 70 | 5 |

To complete product formulation 3382 ml of permeate feedstream was concentrated to dryness under reduced pressure and made up to 2000 ml (90% aqueous 1,3 butylene glycol) and 0.3% (w/w) phenoxyethanol added. The solution was filtered through a 0.45 $\mu$m filter (Whatman) before packaging. The finished oat extract contains 10 ppm of total Avenanthramides.

EXAMPLE 3

Anti-Erythema Testing in Human Subjects

Skin tests were carried out on healthy male and female volunteers
a. 18 to 60 years of age;
b. Fair-skinned with skin types I–III, determined by the following guidelines:
  I Always burns easily; never tans (sensitive)
  II Always burns easily; tans minimally (sensitive)
  III Burns moderately; tans gradually (normal)
  IV Burns minimally; always tans well (normal)
  V Rarely burns; tans profusely (insensitive)
  VI Never burns; deeply pigmented (insensitive)
The following exclusion criteria were followed:
a. Subjects with a history of abnormal response to sunlight;

b. Subjects exhibiting current sunburn, suntan, or even skin tone which might be confused with a reaction from the test material or which might interfere with evaluation of the results of the test;
c. Pregnant or lactating females;
d. Subjects taking medication which might produce an abnormal response to sunlight or interfere with the results of the test;
e. Subjects who regularly use UVA sunbeds; or
f. Subjects exhibiting any visible skin disease which could be considered to affect the purpose or integrity of the study.

Nine (9) subjects who met the inclusion criteria were selected for participation.

A xenon arc solar simulator (Solar Light Sources Philadelphia, Pa.) was used as the source of ultra-violet light. A continuous emission spectrum in the UV range (290–400 nanometres) was utilised during the course of this testing procedure. The lamp output was measured with a UV intensity meter (Model PMA 2100) with the appropriate detector attached.

A Minolta CHROMA METER™ CR-300 (Minolta Corporation Ltd., Osaka, Japan) was used to measure erythema levels. The a* value of the L*a*b* colour notation system is indicative of colour changes in the red-green colour axis. The higher the value, the more intensely red the object being evaluated. Therefore, the a* value was used as a measure of redness (erythema) on the skin surface. An increase in a* values is considered indicative of increased erythema.

On day 1 die minimal erythemal dose (MED) of each subject was determined by a progressive sequence of timed UV light exposures, each of which was graduated incrementally by 25% over that of the previous site. An MED is defined as the time interval or dosage of UV light irradiation sufficient to produce a minimal, perceptible erythema on untreated skin.

On day 2 subjects returned to the laboratory approximately 24 hours after irradiation for determination of their MEDs. The sites were evaluated for erythema according to the following visual scoring criteria:
0=negative, no visible reaction
0.5=minimal erythema
1.0=defined erythema
2.0=moderate erythema
3.0=severe erythema A technician outlined seven 1"×1.5" test-sites areas on each subject's back, between the scapulae and the belt-line, lateral to the mid-line, with a surgical marking pen. Six test sites were designated for the test materials and one for the untreated irradiated control.

The sites were then exposed to UV light 1.5 times the predetermined MED values.

On day 3, approximately 24 hours after irradiation, erythema was evaluated and scored visually by a trained technician using the criteria outlined above. Baseline a* value readings were also taken with the Minolta CHROMA METER™. Three consecutive chroma meter readings were taken and averaged.

Approximately 0.2 ml of test product was applied to the appropriate test site. Approximately 4 hours after product application, the test sites were visually scored and Minolta chroma meter reading taken.

On day 4 the subjects returned to the clinic approximately 24 hours after the product application. The 7 sites were again evaluated for erythema using both the visual grading system and the Minolta CHROMA METER™.

The results were subjected to statistical analysis using t-Test (dependent) to determine if any significant differences were observed in the mean chroma meter a* value readings from baseline (24-hours post-irradiation) to 4 hours post-treatment and 24-hours post-treatment, for each test site. Significance was observed if $p \leq 0.05$.

Product test solutions consisted of oat extract in butylene glycol:water 1:1 w/w adjusted to the required concentration (ppm) of Avenanthramide, The results of testing oat extract in human volunteers are shown in Table 4.

TABLE 4

| Oat Extract Avenan- | | Average a* Value | | | Change from Baseline (%) | |
|---|---|---|---|---|---|---|
| thramide (PPM) | | Baseline | 4 Hours | 24 Hours | 4 Hours | 24 Hours |
| 45.0 | Site #2 | 11.47 | *10.39 | *9.33 | −9.4 | −18.7 |
| 15.0 | Site #3 | 12.47 | *11.03 | *10.18 | −11.5 | −18.4 |
| 5.0 | Site #4 | 12.65 | 11.30 | *10.19 | −10.7 | −19.4 |
| 1.5 | Site #5 | 12.04 | *10.67 | *10.35 | −11.4 | −14.0 |
| 0.5 | Site #6 | 12.42 | *11.10 | 11.54 | −10.6 | −7.1 |
| Untreated Irradiated Control | Site #7 | 13.22 | *12.03 | 12.53 | −9.0 | −5.2 |

Note *denotes statistically significant difference from baseline readings

The tests indicated that the oat extracts were efficient at reducing erythema. The dose response kinetics indicated that between 0.03 and 0.3 ppm the relationship between dose and response was linear. Maximum response was obtained at >0.3 ppm of Avenanthramide.

EXAMPLE 4

Isolation and Purification of an Avenanthramide Fraction

Further to Example 2, the permeate (270 ml) was evaporated under reduced pressure and made-up to 10 mls in 1:1 (v/v) aqueous ethanol. The solution was applied to a LH20 column (100 ml) pre-equilibrated in ethanol:water:acetic acid (40:59:1). The column was washed with 2 Vb of solvent and the resulting fraction discarded. The Avenanthramides were eluted from the column with two bed volumes of 80% aqueous acetone. The sample was evaporated to dryness under reduced pressure and then redissolved in 100 mls of 90% aqueous butylene glycol. The solution was filtered through a 0.45 μm filter (Whatman Inc.) before packaging. The finished, isolated Avenanthramide faction contained 15 ppm of total Avenanthramide.

The results of testing the isolated Avenanthramide fraction, oat extract, and untreated control are shown in Table 5.

TABLE 5

| | | Average a* Value | | | Change from Baseline (%) | |
|---|---|---|---|---|---|---|
| Sample | | Baseline | 4 Hours | 24 Hours | 4 Hours | 24 Hours |
| Isolated Avenanthramide (15.0 ppm Avenanthramide) | Site #1 | 12.62 | 11.95 | *10.74 | −5.3 | −14.9 |

TABLE 5-continued

| Sample | | Average a* Value | | | Change from Baseline (%) | |
| --- | --- | --- | --- | --- | --- | --- |
| | | Baseline | 4 Hours | 24 Hours | 4 Hours | 24 Hours |
| Oat Extract (15.0 ppm Avenan- thramide) | Site #3 | 12.47 | *11.03 | *10.18 | −11.5 | −18.4 |
| Untreated Irradiated Control | Site #7 | 13.22 | *12.03 | 12.53 | −9.0 | −5.2 |

Note: *denotes statistically significant difference from baseline readings

EXAMPLE 5

Rapid Analytical Method for Avenanthramide

High Performance Liquid Chromatography (HPLC) for total Avenanthramides was conducted using a Beckman binary solvent delivery system using 32 KARAT™ analytical software for Microsoft WINDOWS NT™ (Beckman Coulter Inc.,). Avenanthramides were separated on a CSC ODS HYPERSIL™ column (250×4.6 mm, 120 Å, 3 μm) using a C18 guard column (Supelco: Sigma-Aldrich Corporation) at 22 C. A Beckman photodiode array (PDA) detector monitoring from 210–400 nm, and specifically 330 nm was used to detect all Avenanthramides. The peaks of three major Avenanthramides; AF-1, AF-2, and AF-6 were integrated using retention times and spectral data relative to authentic standards synthesized by Dragoco Gerberding & Co. AG.

Extracts were diluted in equal portions with distilled water and stored at 4 C. in amber sample vials before analysis. Twenty (20 μl aliquots) were injected in triplicate. The HPLC solvent system consisted of acetonitrile, and 0.01M aqueous phosphoric acid is shown in Table 6.

TABLE 6

| Time (min.) | Acetonitrile (%) | 0.01M Phosphoric acid |
| --- | --- | --- |
| 0 | 25 | 75 |
| 20 | 37 | 63 |
| 22 | 100 | 0 |
| 25 | 100 | 0 |
| 28 | 25 | 75 |
| 33 | 25 | 75 |

EXAMPLE 6

Large Scale (Commercial) Production of Oat Extract

Method. Hulless oats, 500 kgs (variety NO141-1) frozen overnight at −18 C. The frozen grain was ground through a FITZ MILL® COMMINUTOR® (The Fitzpatrick Company: Elmhurst, Ill.) equipped with a $1/8^{th}$ inch screen to produce a coarse oatmeal (100% passed through a 10 Mesh and <10% passed through a 100 Mesh screen sieve).

The meal was vigorously dispersed in 1500 kg of 50% (w/w) ethanol at 20° C. and mixed for 2–16 hours. The resulting slurry was centrifuged through a decanter centrifuge (Westphalia Separator). The pH of the supernatant was adjusted to pH 2.8±0.5 with hydrochloric acid (17.5% w/w) and stirred for one hour.

The extract was then subjected to ultrafiltration using 5,000 MWCO spiral membrane (21.4 m² Synder Filtration, Vacaville, Calif.).

The sterile permeate was next concentrated using reverse osmosis (RO) membrane filtration (15 m² FilmTec Corporation, Minneapolis, Minn.). Before RO concentration the pH was adjusted to pH 6±0.5). Following concentration the resulting oat extract had an Avenanthramide concentration of between 200 and 1500 ppm. This extract was found to be stable for more than four months with no loss of activity, clarity or other measurable parameters of product quality.

The high Avenanthramide extract was used as a stock solution for direct use in therapeutic or cosmetic formulations, or alternatively, the ethanol:water was replaced with an alternative solvent for example butylene glycol:water or glycerine:water.

EXAMPLE 7

Formulation of Oat Extract Concentrate into Butylene Glycol:Water

A diluent solution was prepared by taking >90% of the required final volume of butylene glycol:water (50% w/w) to which is added the calculated volume of oat extract concentrate. The required volume of concentrate is readily calculated from the values of concentrate Avenanthramide concentration, together with die final desired concentration and volume. Oat extract has been formulated into butylene glycol:water at Avenanthramide concentrations in the range of 15–200 ppm of Avenanthramide.

The product was thoroughly mixed and then heated to 70 C. The product was then passed through an evaporator (Pfaudler, Inc. Wiped Film Evaporator) to remove ethanol. Residual ethanol was tested for using standard gas chromatographic (GC) techniques. Following passage through the evaporator, the butylene glycol:water ratio was checked and adjustments made to account for any loss of water in the evaporator. For cosmetic and therapeutic use the pH of the product was adjusted to pH 6.0–7.5.

Finally, the preservative 2-phenoxyethanol was added (0.3% w/w) to the product. The product was sterilized by membrane filtration. The product Avenanthramide content was then analysed and confirmed to meet the desired product specification.

EXAMPLE 8

Formulation of Oat Extract Concentrate in Glycerine:Water

A diluent solution was prepared by taking >90% of the required final volume of glycerine:water (>30% w/w) to which is added the calculated volume of oat extract concentrate. The required volume of concentrate is readily calculated from the values of concentrate Avenanthramide concentration, together with tile final desired concentration and volume. Oat extract has been formulated into glycerine:water at Avenanthramide concentrations in the range of 15–250 ppm of Avenanthramide, The product was thoroughly mixed and then heated to 70 C. The product was then passed through an evaporator (Pfaudler Wiped Film Evaporator) to remove ethanol. Residual ethanol was tested for using standard gas chromatographic techniques. Following passage through the evaporator, the glycerine:water ratio was checked and adjustments made to account for any loss of water in the evaporator. For cosmetic and therapeutic use the pH of the product was adjusted to pH 6.0–7.5. For functional food/nutraceutical use the pH of the product was adjusted to pH4.0.

Finally, the preservative system consisting potassium sorbate (0.1% w/w) and sodium benzoate (0.1% w/w) was added to the product. The product Avenanthramide content was then analysed and confirmed to meet the desired product specification.

EXAMPLE 9

Hypo-Allergenic Shampoo for Veterinary Use

Table 7 presents an example of a therapeutic shampoo formula falling within the scope of the present invention with amounts provided expressed as weight percent.

TABLE 7

| Phase | Material Description | Supplier | Percent by weight |
|---|---|---|---|
| A | Deionised water | | 45.65 |
| A | Sequestrene NA3T | Ciba-Geigy | 0.05 |
| A | Incromide LR | Croda Inc. | 5.00 |
| A | Standapol ES-2 | Henkel | 28.00 |
| A | Velvetex BA-35 | Henkel | 8.00 |
| A | Polysorbate 20 | ICI | 1.50 |
| B | Hydrolysed Oat Protein | Ceapro Inc. | 8.00 |
| B | Oat Extract | Ceapro Inc./ DRAGOCO Gerberding & Co. AG | 3.20 |
| B | Oat Beta Glucan | Ceapro Inc./ DRAGOCO Gerberding & Co. AG | 0.20 |
| C | Fragrance | | 0.20 |
| C | Kathon CG | Rohn and Haas | 0.20 |

Add ingredients in phase A one at a time with medium agitation at room temperature. Ensure each ingredient is dissolved before adding next. The solution should be clear before going onto phase B. In phase B, add ingredients one at a time to phase A with mixing. Add ingredients in phase C one at a time to the mixing phase AB. Adjust the pH with a 50% solution of citric acid until the pH is 6.5.

To use, the product may be either applied directly to the animal or alternatively, mixed with water in a suitable vessel and applied to the animal by sponging. The product rinses easily ensuring that all surfactant is removed after bathing.

The completed shampoo effectively reduced pruritus in animals. Further, the shampoo reduced shedding and scaling.

EXAMPLE 10

Soothing Formula for Veterinary Use in Treating Otitis

Table 8 presents an example of a pharmaceutical cleansing formula falling within the scope of the present invention with amounts provided expressed as weight percent.

TABLE 8

| Ingredient | % Formula |
|---|---|
| Deionised water | 46.0 |
| Butylene glycol | 48.85 |
| Oat Extract | 4.0 |
| Lactic Acid | 0.8 |
| Malic Acid | 0.2 |
| Methyl Paraben | 0.15 |

The ingredients were added one at a time to a mixing vessel with stirring. Ensure each ingredient is dissolved before adding next. The pH of the finished product was adjusted to 4.0 using 50% malic acid.

The product is for use in cleaning ears in dogs, puppies, cats, and kittens.

To clean the ear, fill the canal with cleanser, flip the ear pinna over, and massage. Take cotton balls and thoroughly remove exudate and dry the accessible portion of the canal. Repeat daily until ear is clean, treat weekly afterwards or as directed by the veterinarian.

Clinical trial results proved the product to be superior in reducing redness associated with otitis and to effectively reduce irritation, promoting the healing of the animal.

Thus, novel methods for producing liquid oat extracts and compositions containing liquid oat extracts are disclosed. Although preferred embodiments of the subject invention have been described in some detail, it is understood that obvious variations can be made without departing from the spirit and scope of the invention defined by the appended claims.

What is claimed is:

1. A method for producing an oat extract having at least 1 ppm avenanthramide, comprising the following steps:
 a. milling whole oats;
 b. extracting the resulting oatmeal with a solvent "comprising water and a primary or a secondary alcohol";
 c. adjusting the pH of the resulting oat extract to <4.0;
 d. membrane filtration of the oat extract with a pH <4.0 through a membrane <$10^4$ MWCO.

2. A method according to claim 1, wherein the primary alcohol is selected from the group consisting of ethanol, methanol, propanol (n-, iso-), butanol (n-, iso-, tert-), and mixtures thereof.

3. A method according to claim 1, wherein the membrane filtration is an ultrafiltration.

4. A method for producing an oat extract containing a minimum of 10 ppm of avenanthramide comprising the following steps:
 a. milling whole oats;
 b. extracting the resulting oatmeal with a solvent "comprising water and a primary or a secondary alcohol";
 c. adjusting the pH of the resulting oat extract to <4.0
 d. membrane filtration of the oat extract with a pH <4.0 through a membrane <$10^4$ MWCO;
 e. adjusting concentration of avenanthramide to >10 ppm.

5. A method according to claim 4, wherein said milling is coarse milling of frozen grain.

6. A method according to claim 4, further comprising concentrating and purifying the product of step d using reverse osmosis.

7. A method according to claim 1, wherein said milling is coarse milling.

8. A method according to claim 1, wherein said milling is coarse milling of frozen grain.

9. A method according to claim 1, further comprising concentrating and purifying the product of step d using reverse osmosis.

* * * * *